(12) United States Patent
Sinyagin (10) Patent No.: US 7,910,789 B2
(45) Date of Patent: Mar. 22, 2011

(54) METHOD FOR TREATING WOUND, DRESSING FOR USE THEREWITH AND APPARATUS AND SYSTEM FOR FABRICATING DRESSING

(75) Inventor: Dmitriy Sinyagin, San Carlos, CA (US)

(73) Assignee: PolyRemedy, Inc., Mountain View ( * ) Notice: Subject to any disclaimer, the term of this patent is extended or adjusted under 35 U.S.C. 154(b) by 1153 days.

(21) Appl. No.: 10/431,888

(22) Filed: May 7, 2003

(65) Prior Publication Data

US 2004/0015115 A1    Jan. 22, 2004

Related U.S. Application Data

(60) Provisional application No. 60/378,635, filed on May 7, 2002.

(51) Int. Cl.
  A61F 13/00    (2006.01)
  A61F 15/00    (2006.01)
  A61L 15/00    (2006.01)
  A61B 5/00     (2006.01)

(52) U.S. Cl. .............. 602/41; 602/43; 602/48; 602/900; 424/443; 424/445; 600/306; 706/924; 700/95

(58) Field of Classification Search ............ 602/43, 602/900, 41, 48–52; 706/924, 932; 424/445–447; 700/95, 96, 117, 130, 134; 600/306
See application file for complete search history.

(56) References Cited

U.S. PATENT DOCUMENTS

| | | |
|---|---|---|
| 2,682,873 A | 7/1954 | Idnis |
| 2,836,178 A | 5/1958 | Barr |
| 3,140,572 A | 7/1964 | Petersen et al. |
| 3,729,892 A | 5/1973 | Aslund et al. |
| 3,811,445 A | 5/1974 | Dostal |
| 4,347,841 A | 9/1982 | Benyó et al. |
| 4,522,203 A | 6/1985 | Mays |
| 4,630,426 A | 12/1986 | Gentry |
| 4,751,133 A | 6/1988 | Szycher et al. |
| 4,869,936 A | 9/1989 | Moskowitz et al. |
| 4,957,795 A | 9/1990 | Reidel et al. |
| 5,000,172 A | 3/1991 | Ward |
| 5,265,605 A * | 11/1993 | Afflerbach ............... 600/300 |
| 5,340,363 A | 8/1994 | Fabo |
| 5,395,305 A | 3/1995 | Koide et al. |

(Continued)

FOREIGN PATENT DOCUMENTS

WO    WO 00/43046    *    7/2000

(Continued)

OTHER PUBLICATIONS

European Search Report, EP 03 72 8787, mailing date May 24, 2006.

(Continued)

*Primary Examiner* — Patricia M Bianco
*Assistant Examiner* — Keri J Nelson
(74) *Attorney, Agent, or Firm* — Fenwick & West LLP (57) ABSTRACT

A method of treating a wound using a customized dressing. In the method, at least one wound characteristic is evaluated. A treatment need as a function of the at least one wound characteristic is determined. A dressing having a dressing characteristic responsive to the treatment need is fabricated and applied to the wound. A dressing for use therewith and an apparatus and system for fabricating the dressing are provided.

21 Claims, 8 Drawing Sheets

U.S. PATENT DOCUMENTS

| | | | |
|---|---|---|---|
| 5,489,437 A | 2/1996 | Marra | |
| 5,520,735 A | 5/1996 | Mulder | |
| 5,520,762 A * | 5/1996 | Rasmussen et al. | 156/216 |
| 5,588,428 A * | 12/1996 | Smith et al. | 600/425 |
| 5,641,501 A | 6/1997 | Cooper et al. | |
| 5,653,699 A | 8/1997 | Reed et al. | |
| 5,681,579 A | 10/1997 | Freeman | |
| 5,741,509 A | 4/1998 | Kushner | |
| 5,757,498 A | 5/1998 | Klein, II et al. | |
| 5,762,620 A | 6/1998 | Cartmell et al. | |
| 5,785,697 A | 7/1998 | Trombetta et al. | |
| 5,891,078 A * | 4/1999 | Turngren et al. | 602/58 |
| 5,899,871 A | 5/1999 | Cartmell et al. | |
| 5,935,363 A | 8/1999 | Gilman et al. | |
| 6,043,408 A | 3/2000 | Geng | |
| 6,051,747 A | 4/2000 | Lindqvist et al. | |
| 6,062,285 A | 5/2000 | Dotta et al. | |
| 6,071,267 A | 6/2000 | Zamierowski | |
| 6,153,215 A | 11/2000 | Samuelsen et al. | |
| 6,245,960 B1 | 6/2001 | Eaton | |
| 6,284,941 B1 | 9/2001 | Cox et al. | |
| 6,297,420 B1 * | 10/2001 | Heincke | 602/41 |
| 6,313,369 B1 | 11/2001 | Schiraldi et al. | |
| 6,420,622 B1 | 7/2002 | Johnston et al. | |
| 6,512,160 B1 * | 1/2003 | Rutsky | 602/41 |
| 6,520,425 B1 | 2/2003 | Reneker | |
| 6,655,112 B1 | 12/2003 | Cremer et al. | |
| 6,662,051 B1 | 12/2003 | Eraker et al. | |
| 6,753,454 B1 | 6/2004 | Smith et al. | |
| 6,765,123 B2 | 7/2004 | de Jong et al. | |
| 6,967,261 B1 | 11/2005 | Soerens et al. | |
| 7,105,058 B1 | 9/2006 | Sinyagin | |
| 7,347,846 B2 | 3/2008 | Hermansson et al. | |
| 2001/0000795 A1 | 5/2001 | Bolian, II et al. | |
| 2001/0003148 A1 | 6/2001 | Coffee | |
| 2002/0133502 A1 | 9/2002 | Rosenthal et al. | |
| 2003/0050794 A1 | 3/2003 | Keck | |
| 2003/0233101 A1 | 12/2003 | Lubock et al. | |
| 2004/0015115 A1 | 1/2004 | Sinyagin | |
| 2004/0059199 A1 | 3/2004 | Thomas et al. | |
| 2005/0149259 A1 | 7/2005 | Cherveny et al. | |
| 2006/0020235 A1 | 1/2006 | Siniaguine | |
| 2006/0034816 A1 | 2/2006 | Davis et al. | |
| 2007/0204691 A1 | 9/2007 | Bogner et al. | |
| 2007/0207688 A1 | 9/2007 | Rasor | |
| 2007/0237812 A1 | 10/2007 | Patel et al. | |
| 2008/0004904 A1 | 1/2008 | Tran | |
| 2008/0077091 A1 | 3/2008 | Mulligan | |
| 2008/0108923 A1 | 5/2008 | Sinyagin | |
| 2008/0108927 A1 | 5/2008 | Sinyagin | |
| 2008/0167594 A1 | 7/2008 | Siniaguine | |
| 2009/0131825 A1 | 5/2009 | Burbank et al. | |
| 2009/0204423 A1 | 8/2009 | DeGheest et al. | |
| 2009/0216553 A1 | 8/2009 | Cellura | |
| 2009/0245603 A1 | 10/2009 | Koruga et al. | |
| 2010/0114256 A1 | 5/2010 | Chan et al. | |

FOREIGN PATENT DOCUMENTS

| | | | |
|---|---|---|---|
| WO | WO 00/43046 A2 | 7/2000 | |

OTHER PUBLICATIONS

Examination Report of the European Patent Office, EP 03 72 8787, dated May 18, 2007.

International Search Report, PCT/US03/14574, mailing date Oct. 1, 2003.

PCT International Search Report and Written Opinion, PCT/US2009/048412, Oct. 13, 2009, 13 pages.

PCT International Search Report and Written Opinion, PCT/US2008/50762. Jun. 25, 2008, 10 pages.

PCT International Search Report and Written Opinion, PCT/US2005/25362, Sep. 1, 2006, 9 pages.

Siniaguine, O., "Automatic System for On-Demand Fabrication of Wound Dressings," 2007, pp. 1-15.

United States Office Action, U.S. Appl. No. 11/972,854, Feb. 2, 2010 14 pages.

United States Office Action, U.S. Appl. No. 11/972,854, Jun. 24, 2009, 8 pages.

United States Office Action, U.S. Appl. No. 11/972,846, Jan. 25, 2010, 12 pages.

United States Office Action, U.S. Appl. No. 11/972,846, Jun. 24, 2009, 8 pages.

United States Office Action, U.S. Appl. No. 12/198,604, Jan. 21, 2010, 30 pages.

United States Office Action, U.S. Appl. No. 12/198,604, Jun. 25, 2009, 12 pages.

United States Office Action, U.S. Appl. No. 12/198,676, Sep. 16, 2009, 8 pages.

United States Office Action, U.S. Appl. No. 11/183,459, May 9, 2008, 9 pages.

United States Office Action, U.S. Appl. No. 10/382,422, May 2, 2005, 16 pages.

U.S. Appl. No. 10/431,058.

U.S. Appl. No. 12/164,451, filed Jun. 30, 2008, Siniaguine.

U.S. Appl. No. 12/196,908, filed Aug. 22, 2008, Siniaguine.

U.S. Appl. No. 12/198,604, filed Aug. 26, 2008, Siniaguine.

U.S. Appl. No. 12/198,676, filed Aug. 26, 2008, Siniaguine.

U.S. Appl. No. 11/183,459, filed Jul. 8, 2005, Siniaguine.

U.S. Appl. No. 12/436,071, filed May 5, 2009, Siniaguine.

International Search Report, PCT/US09/039545, mailing date May 29, 2009.

Written Opinion of the International Searching Authority, PCT/US09/039545.

Canadian Examination Report, Canadian Application No. 2,524,934, Feb. 8, 2010, 3 pages.

European Examination Report, European Application No. 03728787.7, Feb. 26, 2010, 4 pages.

United States Office Action, U.S. Appl. No. 12/198,676, Mar. 12, 2010, 7 pages.

European Examination Report, European Application No. 03728787.7, Nov. 15, 2010, 6 pages.

United States Office Action, U.S. Appl. No. 11/972,452, Dec. 3, 2010, 9 pages.

United States Office Action, U.S. Appl. No. 12/110,228, Oct. 22, 2010, 21 pages.

United States Office Action, U.S. Appl. No. 12/436,071, Oct. 22, 2010, 18 pages.

* cited by examiner

```
┌─────────────────────────────────────────────────┐
│                                                 │
│   Determine a Set of Characteristics of a Wound │
│   (e.g., wound type, size, shape, and depth)    │
│                                                 │
│                                            42   │
└─────────────────────────────────────────────────┘
                         │
                         ▼
┌─────────────────────────────────────────────────┐
│                                                 │
│      Define Properties of a Wound Dressing,     │
│       Based on the Wound Characteristics        │
│                                                 │
│                                            44   │
└─────────────────────────────────────────────────┘
                         │
                         ▼
┌─────────────────────────────────────────────────┐
│                                                 │
│            Fabricate the Wound Dressing         │
│                                                 │
│                                            46   │
└─────────────────────────────────────────────────┘
                         │
                         ▼
┌─────────────────────────────────────────────────┐
│                                                 │
│         Apply the Wound Dressing to the Wound   │
│                                                 │
│                                            48   │
└─────────────────────────────────────────────────┘
```

```
┌─────────────────────────────────────┐
│   Receive Digital Image from the    │
│      Digital Imaging Device         │
│                                     │
│                              62     │
└─────────────────────────────────────┘
                 │
                 ▼
┌─────────────────────────────────────┐
│ Request and Receive Wound Characteristics │
│         Specified by a User         │
│                                     │
│                              64     │
└─────────────────────────────────────┘
                 │
                 ▼
┌─────────────────────────────────────┐
│ Determine a Size and Shape of the Wound, Based │
│  on the Digital Image and the Characteristics  │
│                                     │
│                              66     │
└─────────────────────────────────────┘
                 │
                 ▼
┌─────────────────────────────────────┐
│   Generate a Wound Dressing Specification   │
│     and Send to a Fabrication Device        │
│                                     │
│                              68     │
└─────────────────────────────────────┘
```

METHOD FOR TREATING WOUND, DRESSING FOR USE THEREWITH AND APPARATUS AND SYSTEM FOR FABRICATING DRESSING

CROSS-REFERENCE TO RELATED APPLICATION

This application claims priority to U.S. provisional patent application No. 60/378,635 filed May 7, 2002, the entire content of which is incorporated herein by this reference.

FIELD OF INVENTION

The present disclosure of invention generally relates to wound treatment and systems and methods of designing and fabricating a wound dressing. More particularly, it relates to a wound treatment including fabrication of a dressing adapted to match the wound site.

BACKGROUND

Currently, the common method of wound treatment is to cover the wound with a wound dressing. The wound dressing is manufactured as a precut sheet of multi-layer material of various shapes and sizes. The wound dressing is applied to cover the wound and a portion of the surrounding healthy skin. Sometimes the wound dressing is cut to reduce the size and to better fit the wound size and shape. This reduces the amount of healthy skin covered by the dressing.

Figure 1:
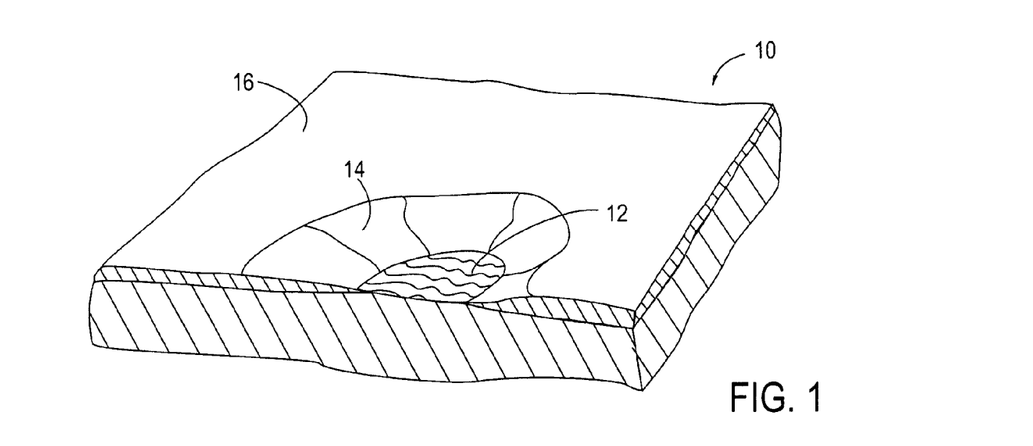
FIG. 1 is an isometric view of a typical wound.

A typical wound commonly has two or more regions or areas, including necrotic, sloughy, bacteria colonized, granulating, epitheliazing, bleeding, exudating, and drying. An exemplary wound 10 has a granulating area 12 having heavy exudates and an epitheliazing area 14 having low exudates, which are surrounded by healthy skin tissue 16 (see FIG. 1). The wound 10 and its areas 12, 14 are usually of irregular shapes. The areas 12 and 14 of the wound 10 typically differ from each other by healing stage, depth, contamination, infection, and tissue stress due to patient body movement. Consequently, covering the whole wound area and surrounding healthy skin with the same dressing type may create adverse conditions for certain areas of the wound or the surrounding skin, which may increase the healing time or even cause adverse effects such as secondary dermatitis.

Accordingly, there is a need in the art for a method for wound care that provides the optimal conditions for wound healing by matching the size, shape, and material properties of a wound dressing to the wound area. There is a further need for a system to produce such a wound dressing.

SUMMARY

According to one embodiment of the invention, a method of treating a wound using a customized dressing is provided. In the method, at least one wound characteristic is evaluated. A treatment need as a function of the at least one wound characteristic is determined. A dressing having a dressing characteristic responsive to the treatment need is fabricated and applied to the wound. A dressing for use therewith and an apparatus and system for fabricating the dressing are provided.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and description are to be regarded as illustrative in nature and not restrictive.

BRIEF DESCRIPTION OF THE DRAWINGS

The accompanying drawings, which are somewhat schematic in many instances and are incorporated in and form a part of this specification, illustrate exemplary embodiments of the invention and, together with the description, serve to explain the principles of the invention.

DETAILED DESCRIPTION

Figure 2:
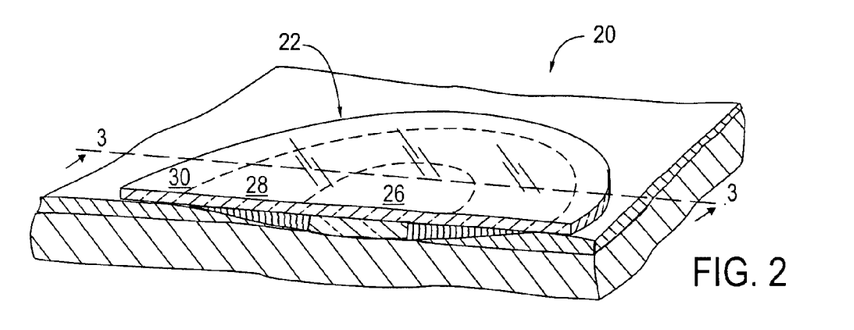
FIG. 2 is an isometric view of a wound covered with a wound dressing according to one embodiment of the present invention.

A wound 20 is covered by an adapted or customized wound dressing 22 (see FIG. 2). The wound dressing 22 may include two or more regions or layers. Each region or layer is customized to match a size and shape of the wound (see FIGS. 2 and 3). It is further customized to address one or more wound healing needs. In one embodiment, the wound dressing 22 includes a first region 26, second region 28, and a backing film 30 (see FIG. 3). The first region 26 of the wound dressing 22 is located generally near a center of the wound dressing 22 and is sized and shaped to generally match or engage the first (e.g., granulating) area 12 of the wound 20. The second region 28 of the wound dressing 22 surrounds the first region 26 and is sized and shaped to generally match or engage the second (e.g., epitheliazing) area 14 of the wound 20.

Figure 3:
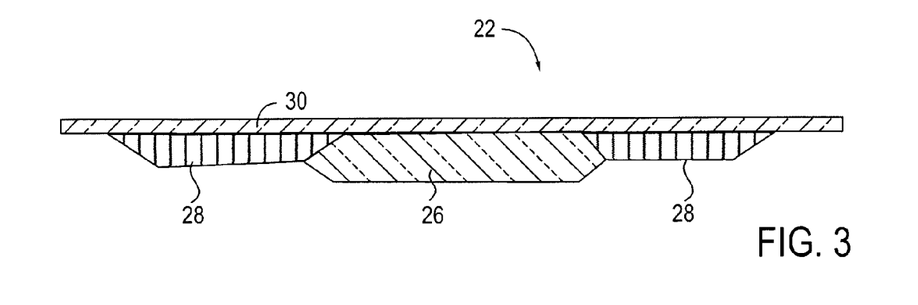
FIG. 3 is a sectional view of the wound dressing taken along the line 3-3 in FIG. 2.

The first and second regions 26 and 28 are typically contiguous to match the contiguous first and second areas 12, 14 of the wound 20. The backing film 30 is positioned on top of the first region 26 and the second region 28 and extends radially outward from the second region 28. The exposed surface of the backing film 30 generally corresponds to the healthy skin surrounding the wound 20. In another embodiment, the wound dressing 22 includes only one of the first region 26, and the second region 28, in combination with the backing film 30. In one embodiment, the first region 26 in the second region 28 include multiple layers of material having differing material properties.

Figure 4:
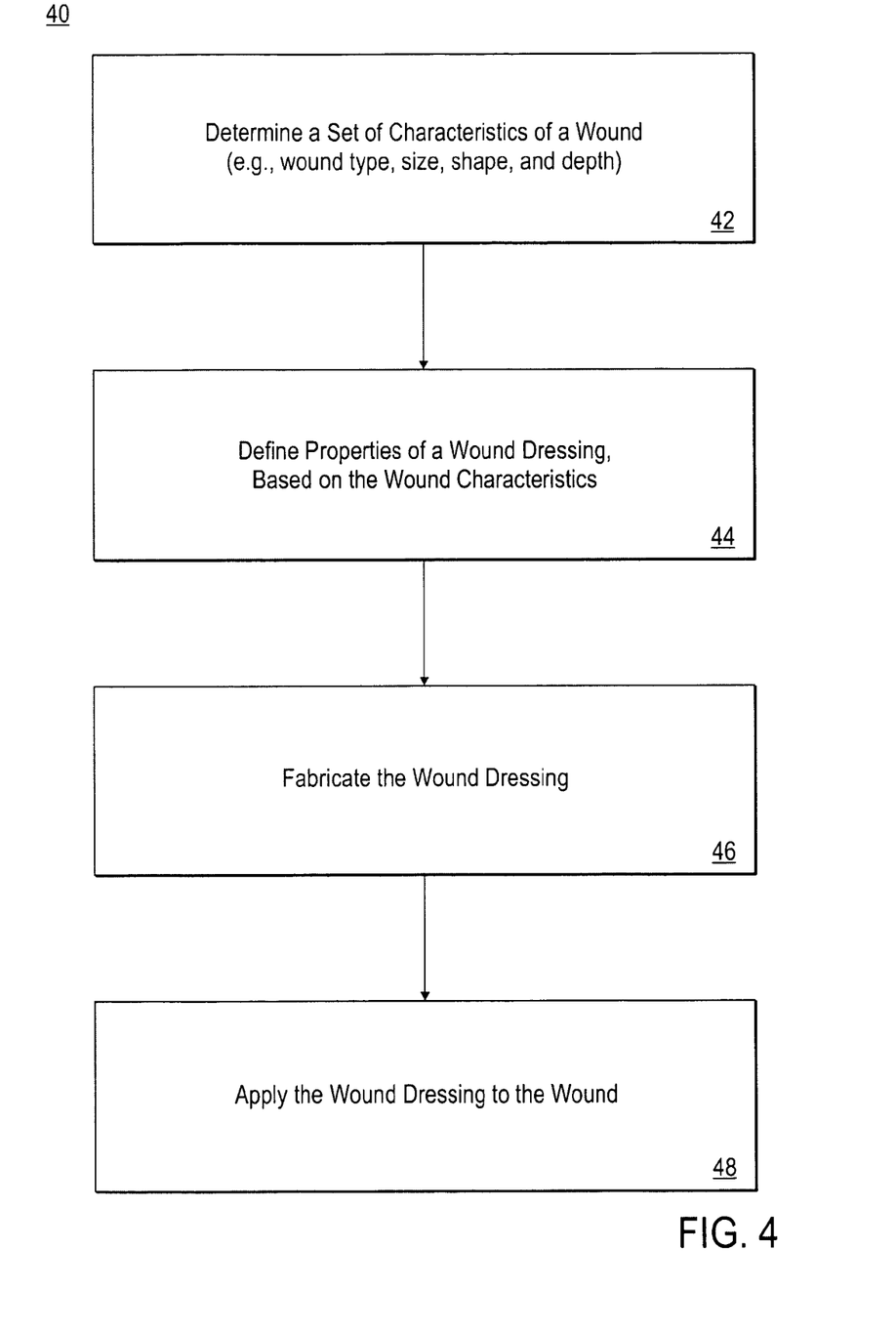
FIG. 4 is a flow chart showing a method of treating a wound using a wound dressing according to one embodiment of the present invention.

The present invention, according to one embodiment, is a method 40 for treating a wound on a patient using the adapted or customized wound dressing 22 (see FIG. 4). In general terms, the method includes evaluating a set of wound characteristics (block 42), defining the properties of a wound dressing based on the wound characteristics (block 44), fabricating the wound dressing (block 46), and applying the wound dressing to the wound (block 48).

Evaluating the characteristics of the wound may be conducted in various ways. The wound characteristics are evaluated and defined in at least two dimensions. In one embodiment, the characteristics are evaluated in three dimensions. Wound characteristics evaluated may include one or more of type of wound, amount of exudate, size, shape, depth, advancement level, bacteria colonization, epitheliazation, sensitivity, severity, health of surrounding skin, periwound properties, and pain level. Wound characteristics may also include one or more of, or the user may use the following, wound severity, the width, length, depth, tunneling, base color of the wound compared to the surrounding skin color, the condition of the wound edge, amount of necrosis, type of exudate, color of exudate, odor of exudate, condition of the periwound area, color or the periwound area, edemic qualities of the periwound area, induration, and granulation. Any other characteristic of the wound can also be evaluated and used to define the attributes of the wound dressing. The wound types may include, for example, burn, cut, ulcer, and abrasion. The exudates may include, for example, none, low, medium, and heavy. Each of the wound characteristics may be evaluated and categorized based on any desired system.

In one embodiment, the evaluation includes generating a two- or three-dimensional map of the characteristics of the wound area. The map may be presented in the form of coordinated points or areas of measured size or coordinated relative to each other or to a common origin point. The coordinates of the local points or areas of the wound may be measured by ruler or digitized using any technique known in the art, including a digital camera or various types of two- or three-dimensional scanners. This map generation process be performed manually by a person or automatically using computer recognition or analytical tools (e.g., chemical, biological, moisture, probing, optical (including UV or IR), or gas), or by some combination thereof. After the mapping technique is specified, the desired wound characteristics or properties are measured for each point in the map. This map may, for example, be stored in a data array including a column specifying the location in the wound and a set of additional columns including data representing each evaluated wound characteristic. The use of discrete data points would facilitate the use of pattern recognition algorithms, as well as tree analysis.

The evaluation process, in one embodiment, also includes an evaluation of certain characteristics of the patient. These patient characteristics may include those characteristics that could affect the success of a treatment routine for the type and severity of the wound. For examples, these characteristics may include allergies, health or immune problems, topography of the body part on which the wound lies, and a color of the surrounding healthy skin.

In one embodiment, the characteristics of the wound dressing are determined solely based on the size and shape of the areas or regions of the wound. In this embodiment, the dimensions of the wound dressing are set to match size, shape, and depth of the wound area. The materials that the wound dressing is fabricated from are determined by the region of the wound to which the material corresponds in another embodiment, the materials from which the wound dressing is fabricated from are further determined by the additional wound characteristics. In yet another embodiment, the materials from which the wound dressing is fabricated are further determined by the patient characteristics.

The defined wound dressing properties or characteristics may include physical, chemical, geometrical, optical, electrical, number of layers, porosity of a layer, thickness, and any other. The determined or assigned characteristics of the wound dressing may include adsorbing capacity, water penetration capacity, water vapor penetration capacity, gas penetration capacity, thickness, material, material form (e.g., continuous film or fiber), number of layers, pharmacological or healing enhancing additives, color, local absence of dressing, and adhesive.

Other characteristics important to the healing process may also be assigned. In other words, based on the wound characteristics, a wound treatment need is determined. For example, a wound having high exudate areas requires a high absorbing and high water evaporation material dressing property. Areas having low exudates and epitheliazing wound areas require low absorbing with limited water permeability material dressing property to keep wound moist environment. The healthy skin area around the wound may be used for the wound dressing attachment with, as an example, medical adhesive. Also, the portion of the wound dressing corresponding to healthy skin must be breathable and suitable for holding an adhesive. This portion of the dressing, for example, may be a porous films or fiber web that is completely permeable for gas/vapor but provides mechanical support for the dressing and attachment to the health skin.

The wound dressing is fabricated once the dimensions and materials of the wound dressing are determined. Fabrication is performed using any known wound dressing fabrication technique.

In one embodiment, at least one wound dressing layer is made from polymer fibers. The layer is fabricated by electrospinning or gas blowing of a polymer solution or melted for localized deposition onto the wound, the support, or underlying dressing layers, according to the wound dressing parameter map. The fibers may have a diameter of from about 0.01 to about 50 microns, depending on chosen parameters of the deposition process.

In one embodiment, the outer layer of the dressing is made from a continuous polymer film. This film may be porous with a pore size small enough to prevent penetration of dust, aerosol, and bacteria. The pore size, in one embodiment, may be from about 0.01 to about 1 micron. The film is made of or coated by an at least partially-hydrophilic polymer. The film thickness is chosen to provide mechanical strength and support to the dressing during transfer from the support and application on the wound. The film thickness, in one embodiment, may be in the range of from about 5 to about 100 microns.

The method for deposition of the porous film may be one of the following: pressure or jet spray, ultrasonic spray, electrodynamic spray in an electrostatic field, droplet placement, and solution or melt dispensing. The film thickness and pore size are controlled by material flow rate, size of droplets during spray, velocity of the droplets colliding with the support, electrostatic field strength, relative velocity of the support movement or dwelling time at the certain point of the dressing, number of passes over the certain point, overlapping of other deposition areas, temperature of the droplets and the support.

A medical adhesive may be applied to areas of the outer layer of the wound dressing extending beyond the area of the wound to assist in attaching the wound dressing to the skin. In this embodiment, the wound dressing map is extended beyond the wound area so that the outer layer with the adhesive corresponds to available healthy skin areas. The wound dressing parameter map may be made so that the wound dressing layer extending beyond the wound area forms strips or ribbon, to be used for wrapping around the patient body (e.g., hand, foot, leg, or finger) for convenient and reliable wound dressing placement and attachment. This may eliminate the need for secondary dressings and attachment enforcing means (e.g., sticky tape, elastic gauze, and compressive wraps). The thickness of these areas may be increased to provide additional strength for compressive dressing application. The strips or ribbons may be designed in the map to include locking features such as loops or hooks. Likewise, the wound dressing parameter map may be developed so that at least one dressing layer is provided with thickened strips or any form grid to provide expansion strength to the dressing for compression application.

One embodiment of the present invention is a computer-based system 50 for evaluating the wound 20, creating a map of wound properties or characteristics, and fabricating and adapted or customized wound dressing 22. In one embodiment, the system 50 includes a digital imaging device 52, a computer or processor 54, and a wound dressing fabrication system 56 (see FIG. 5).

Figure 5:
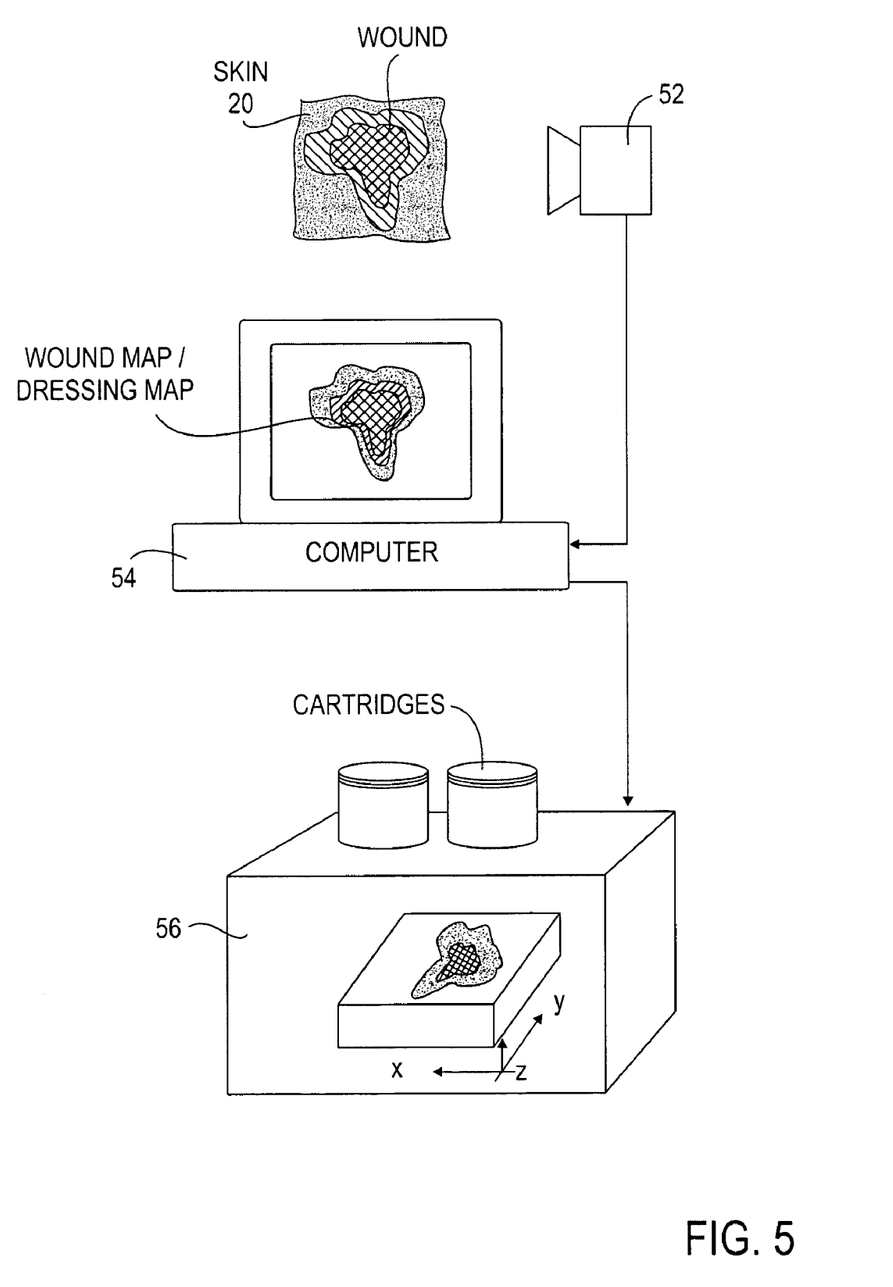
FIG. 5 is a schematic view of a wound dressing fabrication system according to one embodiment of the present invention.

The digital imaging device 52 may be any digital imaging device known in the art, including a digital camera and a digital scanning device. For example, the digital imaging device may be the RAINBOW 3D camera marketed by Genex Technologies, Inc. of Kensington, Md. The digital imaging device 52 is used to generate a digital image of the wound and the surrounding tissue. In one embodiment, the device 52 is used to produce a digital image of the entire body part on which the wound is located. In one embodiment, the system 50 does not include a digital imaging device 52. In this embodiment, the characteristics and dimensions of the wound dressing are specified solely based on information provided by a user of the system 50.

Figure 6A:
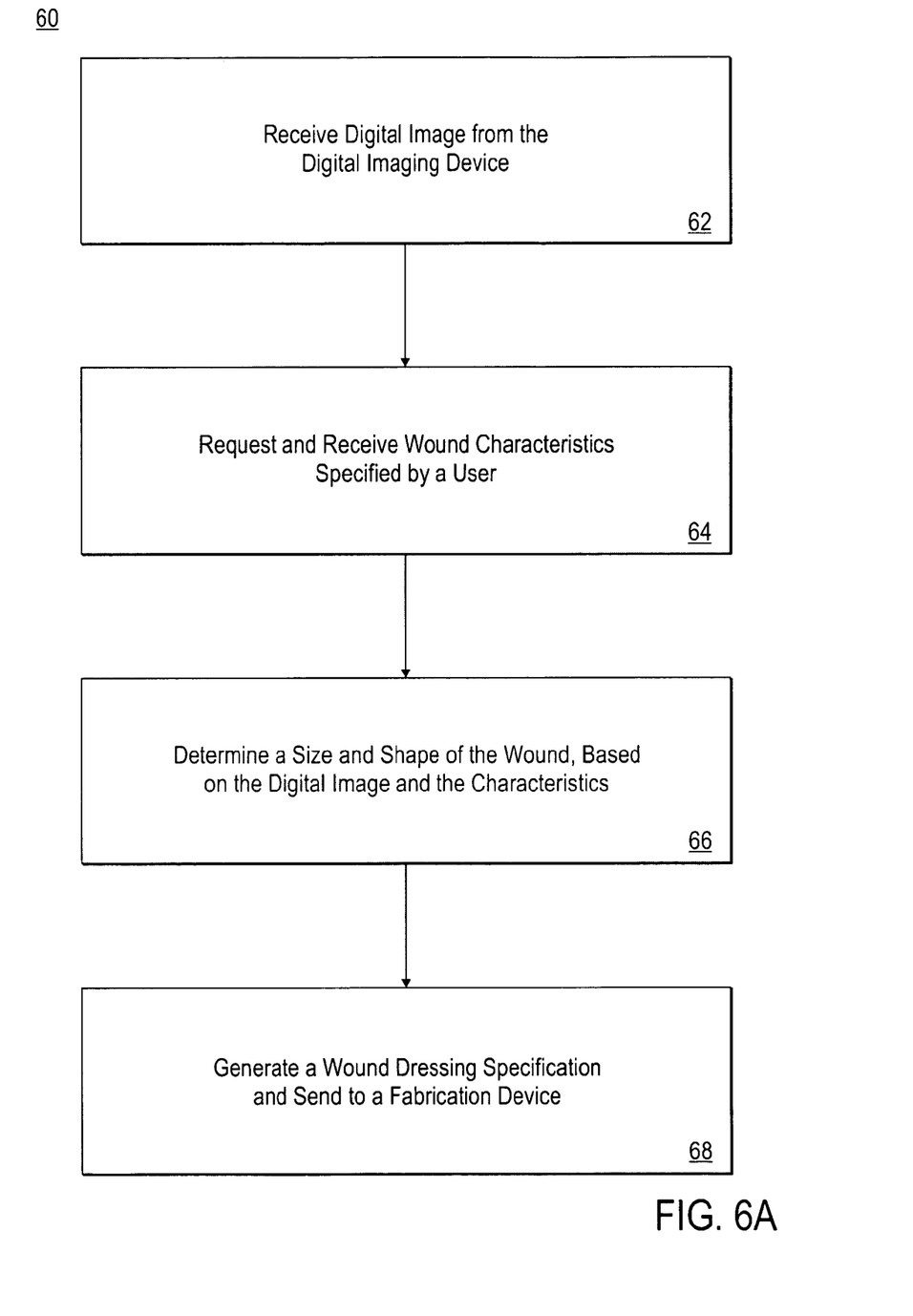
FIGS. 6A and 6B are flow charts illustrating the steps performed by the processor of the system shown in FIG. 5, according to various embodiments of the invention.

The computer or processor 54 is programmed with a software program for receiving characteristics or attributes of the wound 20 and creating a wound dressing map for output to the fabrication system 56. The processor 54 may be programmed with various algorithms, depending upon the needs of a user. In one embodiment, the processor 54 performs a first algorithm 60' (see FIG. 6A). This first algorithm 60' receiving a digital image from the digital imaging device (block 62'), requesting and receiving wound characteristics as specified by a user (block 64'), determining a size and shape of the wound, based on the digital image and the wound characteristics (block 66'), and generating a wound dressing specification, based on the size and shape of the moment, and sending the specification to a wound dressing fabrication device (block 68').

Figure 6B:
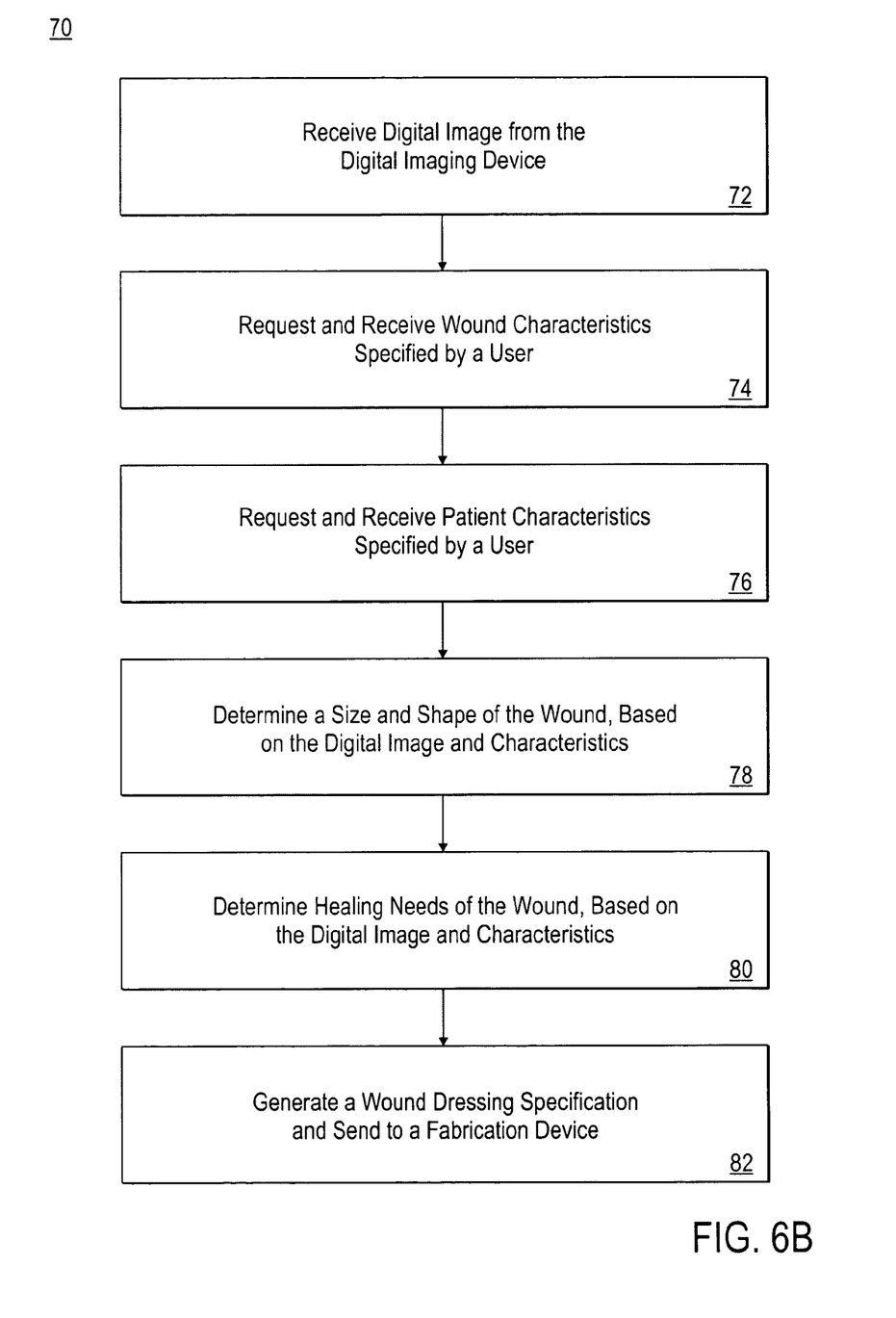

In another embodiment, the processor 54 performs a second algorithm 70' (see FIG. 6B). This second algorithm 70' includes receiving a digital image from the digital imaging device (block 72'), requesting and receiving wound characteristics as specified by the user (block 74'), requesting and receiving patient characteristics as specified by a user (block 76'), determining a size and shape of the wound, based on the digital image and the wound characteristics (block 78'), determining healing needs of the wound, based on the digital image and the wound characteristics (block any), generating a wound dressing specification and sending the specification to a fabrication device (block 82').

In this embodiment, the software program may receives input data concerning any diseases and allergies suffered by the patient. The software program then flags, or issues output alarms if appropriate, patient characteristics that could affect treatment of a wound having the type and severity previously determined by the software program. In one embodiment, the patient data is taken from an electronic file containing the patient's medical history.

In one embodiment, the user chooses desired properties of the dressing for at least some points or zones of the wound characteristic map. This choice may be based on user knowledge of wound healing process or procedures and recommendations available by the time to provide optimal healing conditions for the certain wound areas. The user may also optionally expand the desired dressing properties area (and correspondingly the map) on surrounding healthy skin, for example, for sealing the wound or dressing attachment with a medical adhesive or for protective, cosmetic, marking, aesthetic, and any other purpose. For example, in one embodiment, an outer layer of the dressing may colored or patterned for marking or to match the patient's healthy skin color.

Based on the desired dressing properties map, the user creates a map of dressing properties. As described above, the dressing properties may be physical, chemical, geometrical, pharmacological, biological, optical, electrical, number of layers, porosity of a layer, thickness, and any other. The combination of these parameters at any given point or location of the dressing, define the desired dressing properties map. In one embodiment, the definition of the dressing properties map is done by the user manually. In one embodiment, for example, the user assesses a wound shape (e.g., round, elliptical, triangular, rectangular, trapezoidal, rhomboidal, and narrow strip) and chooses a closest shape from a library of predetermined shapes stored within the processor 54. This may be done for the whole wound or for some areas of the wound and the surrounding skin. The user defines characteristic dimensions of the chosen shape in accordance with the real dimensions of the wound or wound areas. Then the shapes are combined together with coordinated overlapping of these shapes to define the shape of the entire wound area.

In another embodiment, the wound dressing specification or properties map is generated by the processor executing software in automatic or semi-automatic mode, using predetermined experimentally or theoretically dependence of the resulting properties of the dressing on the dressing parameters. If a three-dimensional digitizer or scanner was used for three-dimensional wound or patient body mapping, the image may be flattened to create a two-dimensional wound map and corresponding dressing properties maps.

In another embodiment, characteristics of the wound dressing are determined by comparing wound or patient characteristics to a data set, such as a look-up table, to determine a desired dressing characteristics. The patient characteristics and wound characteristics may be compared to a library of wound dressings properties to generate a selection of proposed wound dressings properties that support the treatment needs or goals.

For a wound dressing including several layers, a separate dressing parameter map may be created for each layer so that the overlapping of the layers and their properties provides the resulting local dressing properties in correspondence with the desired dressing properties map.

The fabrication system 56 uses the dressing parameter map for fabrication of the wound dressing. The fabrication system 56 fabricates the dressing with the characteristics or properties specified by the dressing properties map. In one embodiment, for example, these characteristics include the material, the dimensions, and pharmacological additives.

Proper materials are used in correspondence with the dressing parameter map. Exemplary materials that may be used include polymers (synthetic or natural), biomaterials, pharmacological additives, water, hydrogel or hydrocolloid, adhesives, paints, and fragrances. Any other material that would enhance healing of the wound may also be used in the wound dressing. The selection of an appropriate dressing material for each location within the parameter map may be manually selected by a user, or automatically selected by the processor 54. In one embodiment, for example, the processor 54 selects the material based on the amount of exudate. If the amount of exudate is high, the processor 54 selects the material having a high absorbency. For example, the inner wound dressing layer that will contact the wound may be made from bioabsorbable polymer fibers, including bioabsorbable polymer fibers that are self adherent to a wet wound. If, on the other hand, the amount of exudate is low, the processor 54 may select a moisturizing material. For example, an inner wound dressing layer that will contact the wound may be made from hydrogel having a high concentration of distilled water.

A proper material deposition or application method is used to fabricate the shape or form of the material at every point or area specified in the dressing parameter map. The fabrication methods may include, for example, spraying of polymer solution or melt (with or without electrostatic field or gas flow assistance), jet deposition, dispensing, and any other known or to be invented methods of controllable localized material deposition. Such parameters as the material delivery rate, dwelling time, material temperature, electrical or magnetic field strength and polarity, incident angle, substrate temperature, ambient pressure, temperature and gas or liquid composition, radiation, distance between the material source and the deposition place and any other may be used to meet the requirements of the dressing parameter map. In one embodiment, the dressing is built layer-by-layer using localized material deposition in correspondence with a parameter map for every layer.

The needed thickness of the wound dressing or at least particular layer may be achieved by corresponding variation of the dwelling time over the given point or area, or by variation of the material delivery rate, or by combination of the both methods. The dressing layers may be made by deposition of a substantially homogeneous mixture of any of a variety of hydrophilic and at least weakly hydrophobic polymers, which may be blended with any of a number of medically important wound treatments, including analgesics and other pharmaceutical or therapeutic additives. Materials to fabricate the wound dressing may be in solid-state form and melted, softened, dissolved, mixed, or powdered before and/or during and after deposition.

Such polymeric materials suitable for forming microfibers may include, for example, those inert polymeric substances that are absorbable and/or biodegradable, that react well with selected organic or aqueous solvents, or that dry quickly. Essentially any organic or aqueous soluble polymer or any dispersions of such polymer with a soluble or insoluble additive suitable for topical therapeutic treatment of a wound or for skin treatment or protection may be employed. Examples of suitable hydrophilic polymers include, but are not limited to, linear poly(ethylenimine), cellulose acetate and other grafted celluloses, poly (hydroxyethylmethacrylate), poly (ethylene oxide), and poly vinylpyrrolidone. Examples of suitable polymers that are at least weakly hydrophobic include such as, poly(caprolactone), poly(D,L-lactic acid), poly (glycolic acid), similar co-polymers of theses acids. The present invention provides a method of depositing films or fibers on a surface for other therapeutic or cosmetic reasons, which comprises using the mixture with a biocompatible polymer which may be bioabsorbable or biodegradable polymer such as polylactic acid, polyglycolic acid, polyvinyl alcohol or polyhydroxybutyric acid. Ratio of polymer to solvent in the mixture may vary from 90:10% to 30:70%. Electro conductivity of the mixture may be in the range from 104 to 1010 Ohm/cm.

In one embodiment, other additives, either soluble or insoluble, may also be separately applied or included in the mixtures to be incorporated into the dressing films or fibers. These additives may include medically-important topical additives provided in at least therapeutically-effective amounts for the treatment of the patient or for a skin treatment or protection. Such amounts depend greatly on the type of additive and the physical characteristics of the wound as well as the patient. Examples of such therapeutic and other additives include, but are not limited to, antimicrobial additives such as silver-containing agents, iodine and antimicrobial polypeptides, analgesics such as lidocaine, soluble or insoluble antibiotics such as neomycin, thrombogenic compounds, nitric oxide releasing compounds such as sydnonimines and NO-complexes that promote wound healing, other antibiotic compounds, bactericidal or bacteriostatic compounds, fungicidal compounds, analgesic compounds, other pharmaceutical compounds, fragrances, odor absorbing compounds, and nucleic acids. The additives may also include vitamins, antioxidants, insect and animal repellent, dye, paints, ink, UV, visible, and infrared absorbing and/or reflecting additives, cosmetic additives, paints for fiber coloring, and adhesives. Also, additives for hair treatment, removal, extension, volumizing, protection, coloring, restoration; tattoo and skin defect covering, discoloration, or removal; and skin rejuvenation.

Materials formed of two or more components which have only a short-shelf life when mixed together may be formed in a timely manner using a method embodying the present invention by encapsulating the respective components in respective fibers, particles or microcapsules so that mixing of the various components only occurs when the components are released from the encapsulating material by, for example, leaching through the encapsulating material, rupture by pressure being applied to the encapsulating material, temperature, or degradation, for example bioabsorption or biodegradation, of the encapsulant. Such a method may be used to form, for example, two component adhesives that may be applied separately or simultaneously to a surface as fibers, particles or microcapsules by a method embodying the invention.

The wound dressing fabrication may be done directly on the wound. In this case the dressing parameter map is coordinated and oriented according to the physical position and orientation of the patient body part to be dressed. The system for dressing fabrication may be provided with means for patient body part immobilization. The system may be provided with means to detect the instantaneous position or orientation of the patient body part by optical or X-ray or any other means, and correspondingly provide proper orientation and positioning of the tools for dressing fabrication relative the wound.

The wound dressing fabrication may be done on a support and then transferred onto the wound. The dressing and the wound are properly positioned and oriented relatively to each other to provide acceptably exact application of the wound dressing on the wound. The application may be done manually by the patient, medical personnel or automatically or semi-automatically by a manipulator or robot.

A method and device embodying the invention may also be used for non-medical or skin treatment purposes. For example, coatings of fibers, particles or microcapsules maybe formed on substrates such as paper with good control of the thickness and uniformity of the coating. For example, adhesive may be deposited onto a substrate using a method embodying the invention.

Figure 7:
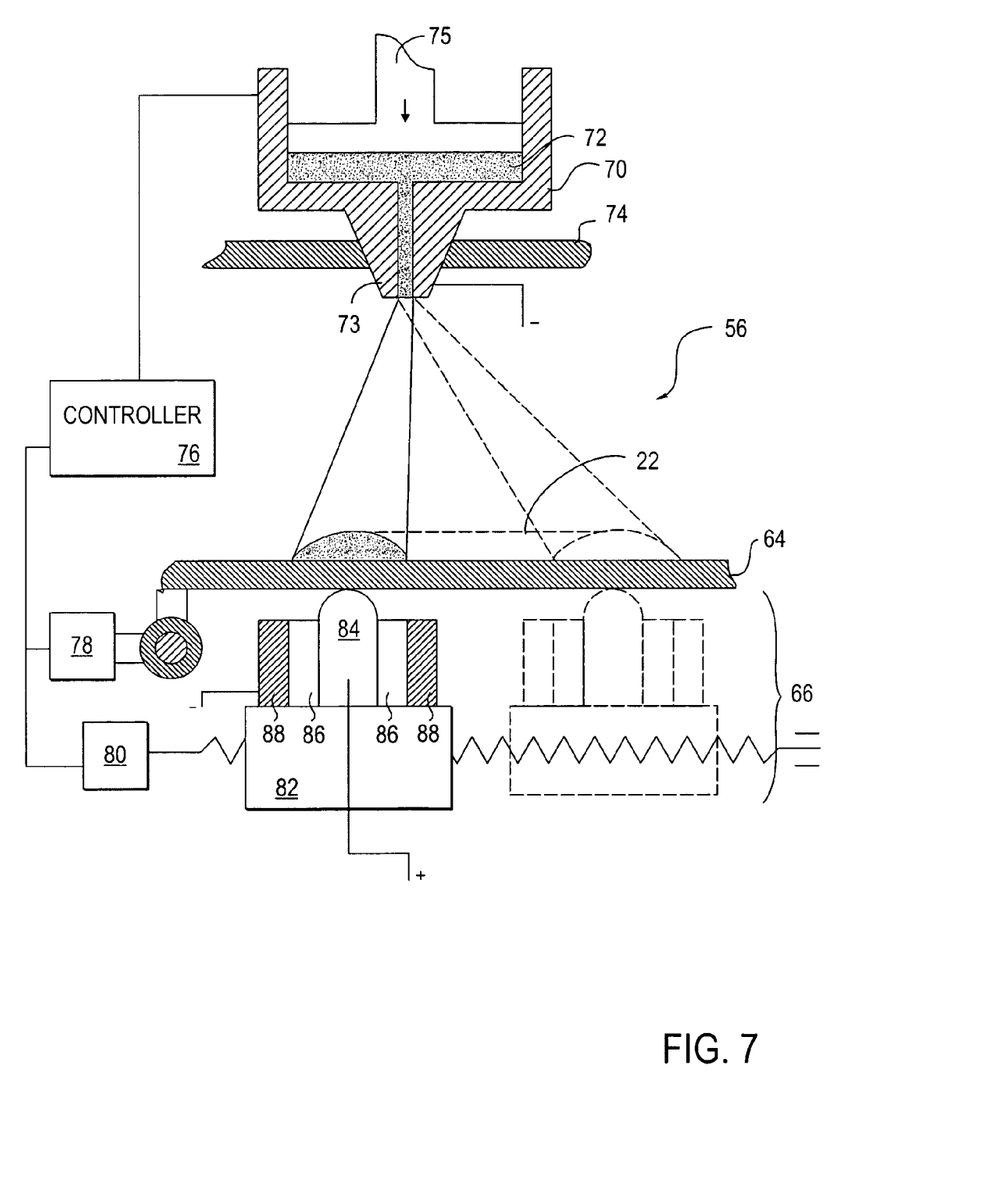
FIG. 7 is schematic view of a portion of a wound dressing fabrication device.

A fabrication device 56 for fabricating the wound dressing 22, according to one embodiment of the invention, includes a localized material deposition source 62, a stage or support 64, and an actuation system 66 (see FIG. 7). The wound dressing 22 is formed on the support 64, by directing material from the deposition source 62 onto the support 64. The actuation system 66 operates to position the support 64, based on the specified wound dressing properties.

The device 56 may be provided with enclosure for sterile and protected dressing manufacturing. The device 56 may be provided with means to sterilize the dressing and internal volume of the system by elevated temperature, irradiation, ultraviolet, or gas for bacteria, spore and microbe elimination. The device 56 may be provided with a sub-system for gas or air recirculation to keep clean and sterile environment with controlled humidity, elimination of solvent vapor or other by-products of material deposition, or ozonating air for sterility. The system interior or the stage may be kept under elevated temperature for sterility or assisting wound dressing fabrication. The system internal volume may be kept under pressure that is higher than ambient atmospheric pressure outside the system to prevent interior contamination by outside air. In one embodiment, the device 56 includes an internal vacuum chamber for dressing fabrication under vacuum or dressing drying or degassing after fabrication.

The deposition source 62 includes a reservoir or cartridge 70 filled with a material 72. The material 72 may be any appropriate material specified by using any of the techniques described above. The material may be in solid, liquid, gel, powder, granule or any other state, or it may be a mixture of different states. The cartridge 70 includes a capillary or outlet 73. The deposition source 62 is held in place by the mounting fixture, 74. The deposition source 62 operates by pushing an actuator 75, which forces the material 72 out of the cartridge 70 through the capillary 73, using any technique known in the art. For example, the actuator 75 may be a piston. The cartridge 70 or the capillary 73, may include a device for controlling a temperature of the structures or of the material 72, such that the material 72 has a temperature that is required by the deposition process. For example, if the material 72 is a powder then it reaches melting temperature upon exiting the capillary 13, as a liquid melt. In one embodiment, the cartridge 70 and capillary 73 are made of electrically conductive material and may be isolated from the mounting fixture 74. An electrical potential may be applied to the capillary 73 or it may be grounded. The mounting fixture 74 may be made of conductive material and held under electrical potential. In one embodiment, the capillary 73 is located from about 0.02 to about 25 cm from the support 64 and faces a deposition surface of the support 64 onto which the wound dressing 22 is fabricated. The internal diameter of the capillary 73, in one embodiment, may be from about 0.1 to about 10 mm. In one embodiment, the deposition source 62 includes two or more cartridges 72 containing different materials 72.

The localized material deposition sources may be any known or to be invented devices that may include, but not limited to, spraying of polymer solution or melt with or without electrostatic field or gas flow assistance, jet deposition, droplet or continuous material placement and dispensing, and any other known or to be invented methods of controllable localized material deposition. In one embodiment, the droplet size is in the range of from about 0.01 to about 50 microns, the fiber thickness is in the range of from about 0.01 to about 20 microns. In one embodiment, the deposition area is controllably changed from about 1 to about 300 mm$^2$.

The support 64 may be selected to provide for low adhesion to the dressing material, including a medical adhesive if it is used for dressing fabrication. In one embodiment, the support 64 forms a part of the final dressing 22. For example, it may provide mechanical rigidity for the dressing to keep the shape, or it may provide support or additional mechanical protection for the wound (to ease the pressure or prevent tissue moving). In other embodiments, the support 64 is a separate component from the dressing 22. In these embodiments the support 64, may serve as part of the packaging over may be discarded after fabrication of the dressing 22. The support for wound dressing fabrication may have a three-dimensional topography that reproduces the patient body three-dimensional topography. That allows manufacturing a wound dressing that fits three-dimensional topographies of the wound or patient body. The stage or support 64 may be include heating or cooling elements to control a temperature during deposition of dressing materials, or for processing after dressing fabrication.

The support 64 may be made as a thin film or plate. It may have lateral dimensions larger than those of the dressing 22. In one embodiment, the thickness of the support 64 is in the range of from about 10 microns to about 2 mm.

The actuation system 66 includes components for positioning the support 64, relative to the deposition source 62. The actuation system 66 may include components for either two or three-dimensional movement of the support 64 (or the deposition source 62). In one embodiment, the actuation system 66 includes a computer or processor 76, a first linear actuator 78 and a second linear actuator 80. The first linear actuator 78 is coupled to the support 64 and the second linear actuator 80 is coupled to a movable platform 82. The movable platform 82 supports a first lower electrode 84. In one embodiment, the first lower electrode 84 is surrounded on either side with a dielectric material 86 and a second lower electrode 88. The second lower electrode 88 may also be surrounded by an additional dielectric material followed by yet another electrode, and so on. The first lower electrode 84 is positioned on the opposite side of the support 64 as the capillary 73. The tip of the first lower electrode 84 may be located close to the support 64, or may touch the surface of the support 64. The tip of the first lower electrode 84 may be made rounded and coated with a material for low friction. The second (and any following) electrode tips may be located close to the support 64 or may even touch the surface of the support 64. The tips of these electrodes may be rounded and may be coated with a material for low friction.

The first linear actuator 78 is coupled to the support 64, such that it causes translation of the support 64 and either an "x" (to the left or right is shown in FIG. 7) or a "y" (Intuit out of the page as shown in figure seven) direction. In one embodiment, two actuators are coupled to the support 64 to cause motion in both directions. Likewise, the second linear actuator 80 is coupled to the movable platform 82, such that it causes translation and either in the "x" or the "y" directions. In one embodiment, two actuators are coupled to the movable platform 82 to cause motion in both directions.

The controller 76 actuates the linear actuator 78 to control position and speed of the support 64 relative to the deposition source 62 according to the wound dressing parameter map. The controller also actuates the linear actuator 80 to control the position in speed of the electrodes 84, 88, relative to the deposition source 62. Using a combined motion of the support 64 and the movable platform 82, the controller can control the position on the support 64 that the material 72 impacts. For example, the controller might control the linear actuator 78 to effect motion in the "x" direction, and control the linear actuator 80 to effect motion in the "y" direction. In another embodiment, for example, one of the support 64 and the movable platform 82 may be fixed, and the other may be used to accomplish motion in both directions. If the support 64 includes actuators for effecting two-dimensional controlled movement along its plane, the first lower electrode 84 may be installed along the line perpendicular to the support 64 surface and originating in the center of the outlet of the capillary 73. The velocity of the first lower electrode 84 may be in the range of from about 0 to about 10 m/sec for thin and porous films.

Other actuation mechanisms known in the art may also be used in the system 56 to effect motion of the support 64 and the movable platform 82. In one embodiment the total relative motion between movable member platform 82 and the support 64 is in the range of from about one to about 400 mm.

The controller 76 also operates to turn activate the deposition source 62 and to control deposition conditions, developed for the particular deposition method, according to the wound dressing properties map.

In one embodiment, the device 56 further includes a third dimension actuator for controlling movement in a third dimension. This actuator may be used for fabricating three-dimensional topography of the dressing, or providing optimal conditions for a specific material deposition method, which may differ for different deposition techniques.

During operation, the system 56, such parameters as the material delivery rate, dwell time, material temperature, electrical or magnetic field strength and polarity, incident angle, substrate temperature, ambient pressure, temperature and gas or liquid composition, radiation, distance between the material source and the deposition place and any other may be used to fabricate a dressing 22 having the properties specified in the dressing properties map. The dressing may be fabricated layer-by-layer using proper relative motion of the support 64 and the deposition sources 62 controlled in correspondence with the dressing properties map for each layer. The thickness of the wound dressing or at least a particular layer may be controlled by a variation of the dwelling time over the given point or area while the proper material delivery source is on, a variation of the material delivery rate, or by a combination of both methods.

To accomplish deposition of the material 72 from the deposition source 62 onto the support 64, an electrical potential is implying between the capillary 73 and the first lower electrode 84, such that the electrical field strength between them in range from about 0.1 to about 10 kV/cm. If the support 64 is made of non-electrically conductive material, the shape and size of the first lower electrode 84 is chosen according to the accuracy of material deposition requirements. The diameter of the first lower electrode may be in range from 0.1 to 100 mm. The second lower electrodes 88 and other additional electrodes may also be electrically connected to a sources of electrical potential relative the capillary 73. These additional electrodes may be placed between the capillary 12 and support 16.

According to one embodiment, the system 56 operates as follows. The material 72 is forced out through the capillary 73 with a flow rate of from about 0.01 to about 50 ml/min. The material 72 is pulled by the electrical field, applied between the capillary 73 and the electrodes 84, 88, and accelerated toward the first lower electrode 84, because of the material 72 is carrying an electrical charge. Depending on the material flow rate, material viscosity, polymer molecular mass, and the electric field strength, the material 72 is reaching the surface of the support 64 in the form of a jet, a flow of droplets or microfibers. Copending U.S. patent application Ser. No. 10/382,422, filed Mar. 5, 2003, entitled "Method and Apparatus for Forming a Microfiber Coating," which is hereby incorporated by reference in its entirety, discloses one system that could be used as the device 56 for fabricating the wound dressing.

The size of the deposition spot is defined by the size of the first lower electrode 84 and electrostatic repelling of the droplets or micro-fibers from each other. The deposition spot size may be controlled by the potential, polarity, and positioning of the second lower electrodes 88 and any additional electrodes. The closer the potential of the second lower electrodes 88 and any additional electrodes to the potential of the first lower electrode 84, the wider the deposition zone. If the potential of the second lower electrodes 88 and any additional electrodes is close to the potential of the capillary 73, the material deposition will be more concentrated over the first lower electrode 84. The type and thickness of the dielectric 86 is chosen to prevent the electrical breakdown between the electrodes. In various embodiments, the dielectric may be Teflon or ceramic.

Moving the support 64 relative the capillary 73, the second electrode 17, or both, leaves a trace of deposited material on the surface of the support 64. A continuous layer of material may be achieved by proper two-dimensional scanning and overlapping the scans or traces of the deposited materials. If the dressing layer is made by several consequent passes over the same area then the overlapping may be optimized experimentally with a few simple measurements of thickness uniformity over the resulting layer.

Controllable motion of the first lower electrode 84 caused deflection of the flow of material so that the material deposition spot is moved along the surface of the support 64 without moving the support 64. The deflection may reach about 40 degrees from the perpendicular to the surface of support 64. The morphology of the deposited layer may be changed due to incident angle change so the acceptance of the resulting layer properties has to be checked experimentally. The material flow rate and electrical field strength may be changed as a function of angular position of the first lower electrode 84 to partially compensate for the material travel time variations and, possibly, properties of the material upon reaching the surface. The larger the angular position of the first lower electrode 84, the larger the electric field between the capillary 73 and the first lower electrode 84.

Porosity of the continuous film can be increased by reducing the material flow rate, reducing the electrical field strength, increasing the velocity of the first lower electrode 84, or reducing the film thickness. The pattern of motion of the support 64 may be controlled to fabricate a mesh- or web-like film layer. A skilled artisan will be able to readily determine the necessary combination of parameters for the given material.

In one embodiment, the outer layer of the wound dressing 22 is the first layer deposited on the support 64, which minimizes potential contamination transfer from the support to the internal wound dressing layer that will contact the wound 20. In another embodiment of the invention, the inner layer of the wound dressing 22, which will contact the wound 20 is the first layer deposited on the support 64, which minimizes potential contamination transfer from the ambient environment to the internal wound dressing layer.

The wound dressing fabrication may be done on a support and packaged for storage before use. The package is sterile and hermetic. The package may be vacuumed or filled with a gas to provide dry or inert or non-oxidizing ambient inside the package. In one embodiment, the support for the wound dressing application is at least partially a part of the wound dressing package. The manufactured dressing may be additionally placed in a water vapor, water, contamination impermeable bag with moisture absorbent.

The system may be provided with a sub-system for packing the fabricated dressing in a sterile and hermetic package. Any known or to be invented means and mechanisms for packaging may be used like bagging, wrapping in a film with the following thermo-compress sealing, etc. The auxiliary support may be at least a part of the package and made of the packaging material. The packaging material may be supplied in form of roll or stack of a film, or may be fabricated by spraying or extrusion in the system by any known or to be invented method and apparatus.

Figure 8:
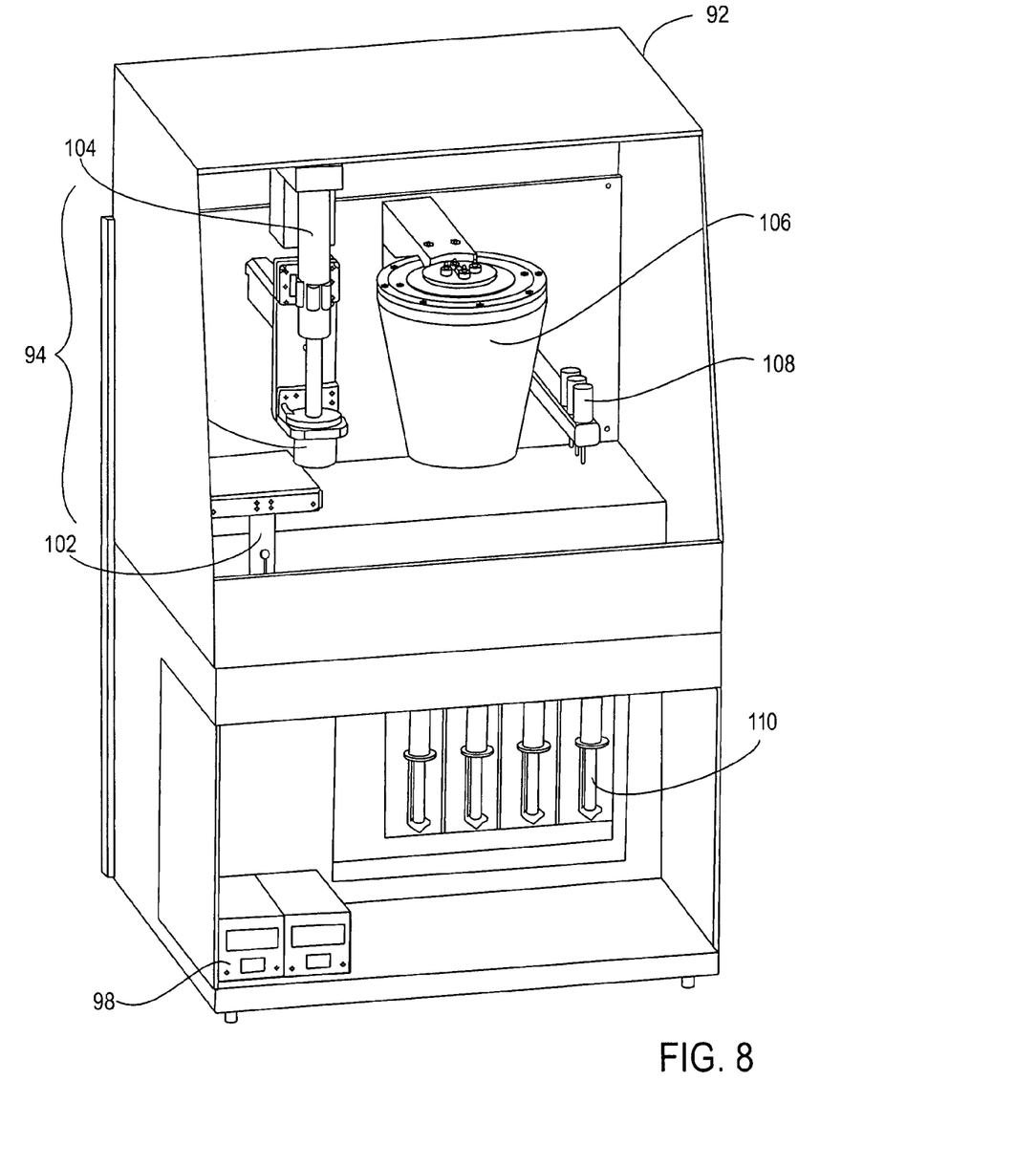
FIG. 8 is an isometric view of a device for fabricating a wound dressing according to one embodiment of the present invention.
Figure 9:
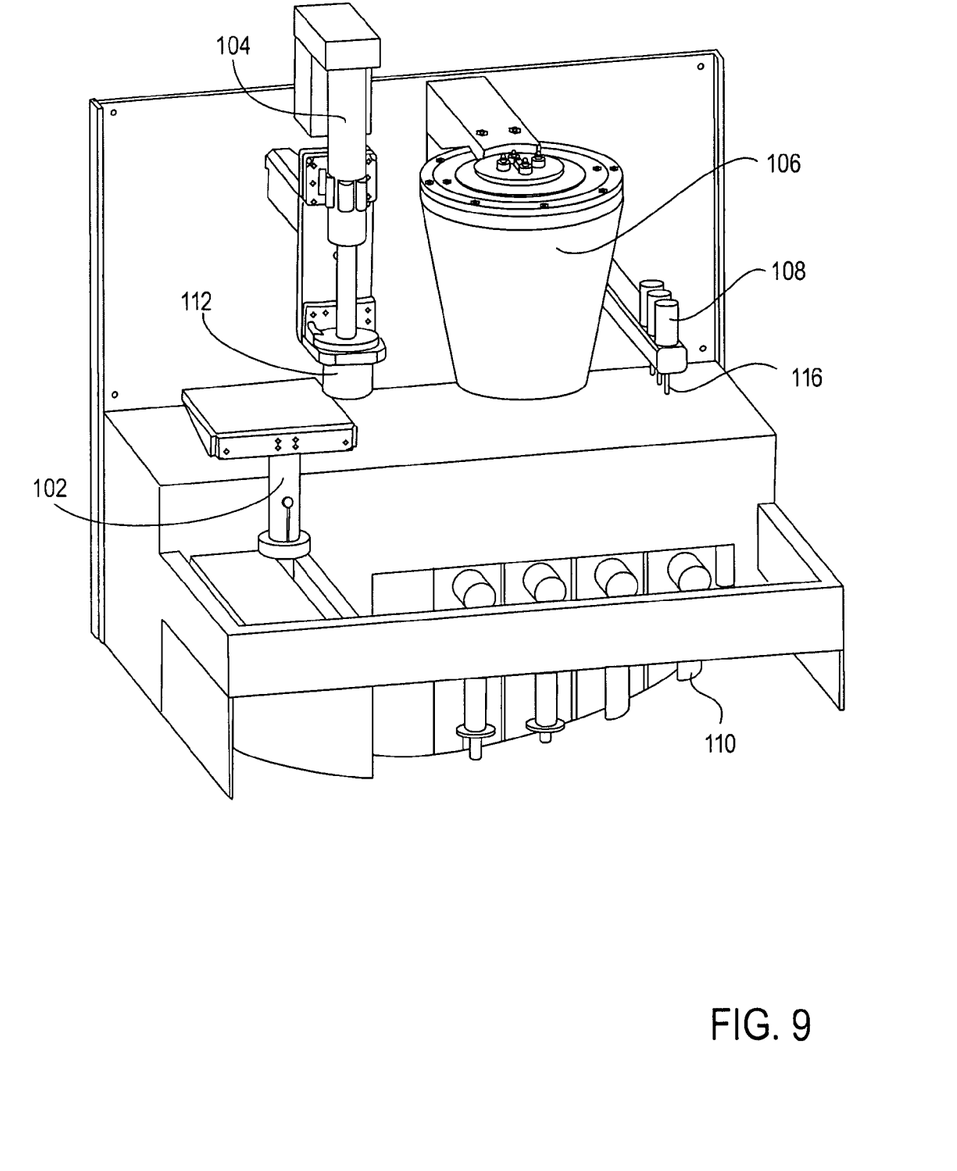
FIG. 9 is a partial isometric view the device of FIG. 8.

Another embodiment of the present invention is an apparatus 90 for wound dressing fabrication (see FIGS. 8 and 9). The apparatus 90 includes a housing 92, deposition tools 94, in deposition table 96, and a controller 98. The housing 92 may be a hermetic enclosure that provides a protected environment for the dressing fabrication. In FIGS. 8 and 9, the housing 92 is shown without front panels for better visibility of the components. The ambient pressure inside the enclosure may be kept positive relatively the atmospheric pressure to prevent penetration of the potentially contaminated air from outside. The enclosure interior may be provided with short wave ultra-violet lamps (not shown) for in-situ sterilization of the internal volume and dressing components.

The deposition table 96 includes a two (x,y) or three (x,y,z) dimensional motorized stage 102. The deposition table 96 is installed inside the housing 92. The deposition table 96 may be made of conductive material and provided with means for temperature stabilization. The deposition tools 94 include a melt film extruder 104, a microfiber with electro-spinner 106, and an applicator 108. The melt film extruder 104 and the electro-spinner 106 are used to fabricate the main dressing components. For example, they can be used to fabricate the backing film and the hydrophilic micro-fiber layer.

Cartridges 110 may hold the polymers and/or therapeutic adjuvants, that are necessary for the wound dressing fabrication (including any of the materials identified above). The cartridges 110 include displacement pumps for controlled delivery of the materials to the deposition tools 94. The controller 98 controls these displacement pumps along with the motion of the deposition table 96.

The melt film extruder 104 is used for fabrication of the backing film of the wound dressing. It includes a barrel 112, filled with the polymer and heated to the temperature recommended for extrusion of that polymer. For example, polyurethane PELLETHANE, available from Dow Chemical, Inc. is extruded at a recommended temperature of from 190° C. to 210° C. The barrel 112 has an outlet slot or orifice at its bottom for the polymer extrusion under pressure created by the actuator 114. During film extrusion, the outlet orifice faces the table 96 and leaves the thin film on its surface in accordance with the pattern programmed for the motorized stage 102.

The electro-spinner 106 is used for fabrication of the dressing microfiber layer using a fiber electro-spinning technique, such as is described in application Ser. No. 10/382,422, entitled, "Method and Apparatus for Forming a Microfiber Coating," which has been incorporated by reference herein. In one embodiment, the microfibers are deposited onto the table 96 surface within an area having a diameter of about 20 mm. Programmed motion of the motorized stage 102 is used to cover larger or irregular shape areas of the dressing.

The applicator 108 may be used for application of hydrogel or therapeutic adjuvants or medical adhesive according to the dressing design requirements by dispensing the substances through the capillaries 116. The substance flow rate is provided by the corresponding displacement pumps 110.

Example

The device 56 has been used for fabrication of a two layer wound dressing having a rectangular outer layer with a size of about 100 by 80 mm and a round internal layer having a diameter of about 50 mm. The electro-hydrodynamic method of microfiber deposition, described above, has been used for both the inner layer and outer layer with changes of material flow rate and electrostatic field value.

A mixture of polyvinilpirralidone (M=360,000) and poly-d,l-lactide (M=150,000), in ratio 1:10, and 80% of solvent ethyl acetate has been used. Flow rate of the mixture was 1 mL/min for the inner dressing layer and 2.5 mL/min for the outer dressing layer. Electrical field strength between the capillary and grounded support was 1.5 kV/cm for the inner dressing layer and 0.5 kV/cm for the outer dressing layer. The distance between the cartridge outlet and the surface was 10 cm. The velocity of the support relative the capillary was 0.5 cm/sec and scanning overlapping was 70%. The internal dressing layer was fabricated as a micro-fiber layer with thickness 1 mm and with size of the micro-fibers about 0.2 micron. The outer dressing layer was fabricated as a continuous film with a thickness of 20 microns and porosity less than 0.5 micron. The internal layer provides wound exudate absorbing properties and transport of the exudate to the external layer. The external layer allowed evaporation of the water from the internal layer to keep balanced moist environment over the wound. Due to its porosity, the outer layer allowed air supply to the wound and, at the same time, prevented contamination and infection of the wound by protecting it from the dust and aerosols that may carry bacteria.

As can be seen from the foregoing, a method of treating a wound using a customized dressing has been provided in one embodiment of the invention. In the method, at least one wound characteristic is evaluated. A treatment need as a function of the at least one wound characteristic is determined. A dressing having a dressing characteristic responsive to the treatment need is fabricated and applied to the wound.

In another embodiment of the method, a method of fabricating a dressing to treat a patient having a wound with at least first and second contiguous regions is provided. The method includes the step of evaluating the wound characteristics of the first region of the wound. The size and shape of the first region of the wound is determined and a dressing having a first portion with a size and shape corresponding to the size and shape of the first region and made from a first material for enhancing treatment of the wound characteristics of the first region of the wound is fabricated.

In another embodiment of the invention, a wound dressing for treating a patient having a wound with at least first and second contiguous regions surrounded by skin is provided. The dressing includes a laminate structure having a first portion made from a first material adapted for engaging the first region of the wound and a second portion made from a second material different than the first material adapted for engaging the second region of the wound. The laminate structure includes an adhesive layer for adhering the laminate structure to the skin of the patient.

In a further embodiment of the invention, a system for fabricating a wound dressing for treatment of a wound is provided. The system includes assessment means for assessing a plurality of wound characteristics associated with the wound, a processor for determining a set of parameters of the wound dressing, based on the plurality of wound characteristics, and fabrication means for fabricating the wound dressing based on the set of parameters.

In another embodiment of the invention, an apparatus is provided for fabricating a wound dressing. The apparatus includes a stage having a fabrication surface, a deposition source of a material directed toward the stage, and at least one controller for controlling a relative position between the deposition source and the stage based on a set of characteristics of the wound. The controller is coupled to the source for activating the source based on the set of wound characteristics and the relative position between the source and the stage.

Although the present invention has been described with reference to exemplary embodiments, persons skilled in the art will recognize that changes may be made in form and detail without departing from the spirit and scope of the invention. In particular, the coatings produced according to the present-invention are not necessarily limited to those achieved using the apparatus described. Thus, the scope of the invention shall include all modifications and variations that may fall within the scope of the claims.

I claim:

1. A system for fabricating a wound dressing customized for a wound, the system comprising:
   one or more actuators within the system, the one or more actuators configured to cause relative motions between materials for fabricating the customized wound dressing; and
   a controller configured to receive wound dressing specification defining characteristics of the customized wound dressing, the characteristics comprising at least a shape of the customized wound dressing, the controller connected to the one or more actuators to control the one or more actuators based on the wound dressing specification to shape and prepare the customized wound dressing as defined by the wound dressing specification.

2. The system of claim 1, wherein the wound dressing specification is received from a processor that generates the wound dressing specification based on an image received from a digital camera or optical digitizer.

3. The automated system of claim 1, further comprising:
   a stage having a fabrication surface on which the customized wound dressing is fabricated;
   an actuator for moving the stage according to commands from the controller; and
   a housing for enclosing at least the stage and the actuator for moving the stage.

4. The system of claim 3, further comprising:
   a first deposition source for depositing a first dressing fabrication material on the stage; and
   a second deposition source for depositing a second dressing fabrication material on the stage.

5. The system of claim 1, wherein the wound dressing specification defines a plurality of dressing zones, each wound zone associated with one or more corresponding wound dressing parameters for a wound zone.

6. The system of claim 5, wherein at least one of the wound dressing parameters represents a shape predefined in a library of predetermined shapes.

7. The system of claim 6, wherein: said library of predetermined shapes comprises at least one of circle, ellipse, triangle, trapezoid and rhomboid.

8. The system of claim 6, wherein the wound dressing specification further defines a dimension of the customized wound dressing.

9. The system of claim 5, wherein:
   said plurality of wound zones comprise at least one of an exudating wound zone and a drying wound zone.

10. The system of claim 9, wherein the wound dressing specification comprises wound dressing parameters for a wound zone, the wound dressing parameters specifying at least one of:
    porosity of a layer in a dressing zone corresponding to the wound zone;
    exudate absorbing capacity of the dressing zone;
    an amount of a pharmacological additive to be contained in the dressing zone;
    moisture evaporating capacity of the dressing zone;
    water vapor penetration capacity of the dressing zone;
    gas penetration capacity of the dressing zone; and
    pharmacological additives included in the dressing zone.

11. The system of claim 5, wherein the wound dressing specification defines shapes and locations of two or more dressing zones corresponding to two or more wound zones of the wound, wherein the two or more wound zones comprise at least one of: a granulating wound zone, an epitheliazing wound zone, a necrotic wound zone, a sloughy wound zone, a bacteria colonized wound zone, a bleeding wound zone, an exudating wound zone, and a drying wound zone.

12. The system of claim 1, wherein the wound dressing specification further defines materials to be added in the customized wound dressing.

13. The system of claim 1, wherein the wound dressing specification further defines a number of material layers in the customized wound dressing.

14. The system of claim 1, wherein the wound dressing specification further defines an exudate absorbing capacity of a material in the customized wound dressing.

15. The system of claim 1, wherein the wound dressing specification further defines a water penetration capacity or a water vapor penetration capacity of a material of the customized wound dressing.

16. The system of claim 1, wherein the wound dressing specification further defines a gas penetration capacity of a material in the customized wound dressing.

17. The system of claim 1, wherein the wound dressing specification further defines materials of the customized wound dressing.

18. The system of claim 1, wherein the wound dressing specification further defines whether a material in the customized wound dressing is a fibrous film or a continuous film.

19. The system of claim 1 further comprising:
    a packaging system for packing the customized wound dressing in a package after the customized wound dressing is fabricated in accordance with the wound dressing specification.

20. The system of claim 19, wherein:
    the packaging system packs the fabricated wound dressing using packaging material from a roll of packaging material.

21. The system of claim 1 wherein the wound specification defines a plurality of dressing zones, each dressing zone corresponding to a wound zone classified based on exudate, type of exudate, color of exudate, or odor of exudate.

* * * * *

UNITED STATES PATENT AND TRADEMARK OFFICE
CERTIFICATE OF CORRECTION

| | |
|---|---|
| PATENT NO. | : 7,910,789 B2 |
| APPLICATION NO. | : 10/431888 |
| DATED | : March 22, 2011 |
| INVENTOR(S) | : Dmitriy Sinyagin |

It is certified that error appears in the above-identified patent and that said Letters Patent is hereby corrected as shown below:

Column 15, line 43, after "The" delete "automated".

Signed and Sealed this
Twenty-fourth Day of May, 2011

David J. Kappos
*Director of the United States Patent and Trademark Office*